United States Patent [19]

Harris

[11] 4,066,712

[45] Jan. 3, 1978

[54] REFORMING PROCESS USING CHROMIUM TRIOXIDE-GRAPHITE INTERCALATION CATALYST

[75] Inventor: Jesse R. Harris, Bartlesville, Okla.

[73] Assignee: Phillips Petroleum Company, Bartlesville, Okla.

[21] Appl. No.: 616,720

[22] Filed: Sept. 25, 1975

[51] Int. Cl.$^2$ ............ C07C 5/22; C07C 15/00
[52] U.S. Cl. ............... 260/668 D; 208/134; 252/447; 260/673; 260/673.5
[58] Field of Search ............... 260/643.5, 673, 668 D; 208/134; 252/447

[56] References Cited

U.S. PATENT DOCUMENTS

| | | | |
|---|---|---|---|
| 2,418,309 | 4/1947 | Matuszak et al. | 252/210 |
| 2,734,874 | 2/1956 | Drake et al. | 252/447 X |
| 2,888,497 | 5/1959 | Pitzer | 260/680 |
| 2,898,388 | 8/1959 | Maloney et al. | 260/673.5 |
| 3,001,930 | 9/1961 | White et al. | 208/136 |
| 3,446,865 | 5/1969 | Roth et al. | 260/673.5 X |
| 3,804,916 | 4/1974 | Lalancette | 260/666 A X |
| 3,812,028 | 5/1974 | Wennerberg et al. | 252/447 X |
| 3,830,753 | 8/1974 | Ichikawa et al. | 252/441 |
| 3,835,067 | 9/1974 | Schneider | 252/447 |
| 3,840,566 | 10/1974 | Lalancette | 252/447 X |
| 3,925,495 | 12/1975 | Rodewald | 260/666 P |
| 3,981,794 | 9/1976 | Eberly | 260/673.5 X |
| 3,984,352 | 10/1976 | Rodewald | 252/447 X |

OTHER PUBLICATIONS

Can. J. of Chem., 50, 3058–3062 (1972).
Australian J. of Chem., 9, 201–205 (1956).
Memoires Presentes a LaSociete Chimique, pp. 177–180.
Carbon, 1974, vol. 12, pp. 199–208.

Primary Examiner—Robert V. Hines
Assistant Examiner—Thomas A. Waltz

[57] ABSTRACT

Nonaromatic hydrocarbons are converted to aromatic hydrocarbons by contacting with a molecular chromium trioxide-graphite intercalation catalytic compound under dehydrocyclization conditions of temperature and pressure. In one embodiment, normal hexane is converted to benzene in the presence of a graphite-chromium trioxide interlayered complex with good conversion and high selectivity.

9 Claims, No Drawings

REFORMING PROCESS USING CHROMIUM TRIOXIDE-GRAPHITE INTERCALATION CATALYST

This invention relates to reforming hydrocarbons. In accordance with another aspect, this invention relates to the dehydrocyclization of nonaromatic hydrocarbons in the presence of a catalyst which is a graphite-chromium trioxide interlayered compound. In accordance with a further aspect, this invention relates to the reforming of naphthas from nonaromatic hydrocarbons by contacting them with a catalyst consisting of a molecular chromium trioxide-graphite intercalation compound whereby good conversion of the feed hydrocarbon is realized with high selectivity to desired components.

Accordingly, an object of this invention is to provide an improved hydrocarbon conversion process whereby the yield of converted hydrocarbon is increased.

A further object of this invention is to provide an improved process for the reforming of naphthas.

Another object of this invention is to provide a catalyst that is active for the dehydrocyclization of nonaromatic hydrocarbons.

Other objects, aspects, and the several advantages of the invention will be apparent to those skilled in the art upon reading the specification and the appended claims.

In accordance with the invention, nonaromatic hydrocarbons are dehydrocyclized to aromatic hydrocarbons by contacting nonaromatic hydrocarbon-containing feed with a molecular chromium trioxide-graphite intercalation catalytic compound under dehydrocyclization conditions of temperature and pressure.

In accordance with a specific embodiment, normal hexane is converted to benzene at low pressure with substantially complete conversion and high selectivity of the paraffin to aromatic by contacting with a chromium trioxide-graphite intercalate complex catalyst.

In accordance with a more specific embodiment of the invention, nonaromatic hydrocarbons are converted to aromatic hydrocarbons by dehydrocyclization in the presence of a chromium trioxide-graphite intercalate complex catalyst prepared by heating a mixture of chromium trioxide and graphite at an elevated temperature and for a period of time sufficient to form a chromium trioxide-graphite intercalate complex having a weight ratio of chromium trioxide to graphite of about 0.01:1 to about 2.5:1.

The catalyst employed in the invention consists of chromium trioxide and graphite wherein the chromium trioxide is intercalated in the graphite. The graphite-chromium trioxide intercalate complex is a known compound which can be prepared in several ways. (Analysis of the compound by X-ray diffraction indicated that the graphite lattice is expanded somewhat compared to untreated graphite, thus allowing insertion of the chromium trioxide.) Based upon laboratory data reported hereinbelow, the different methods of preparing the graphite-chromium trioxide intercalate complex are not equivalent, based on dehydrocyclization results. In accordance with one method of preparing the graphite-chromium trioxide intercalate complex (dry method), and the only method found so far in preparing an intercalate effective as a catalyst for dehydrocyclization, a mixture of anhydrous chromium trioxide and graphite are physically mixed and heated at an elevated temperature for a period of time sufficient to form a graphite-chromium trioxide interlayered compound, i.e., about one hour to about 60 hours or more, then the resulting compound is washed to remove unreacted chromium trioxide and dried by heating. The temperature maintained while heating the mixture of chromium trioxide and graphite is ordinarily in the range of about 175° C to about 400° C. In preparing a complex the weight ratio of chromium trioxide to graphite will ordinarily be about 0.01:1 to about 2.5:1. In accordance with one specific method of preparation, anhydrous chromium trioxide and graphite in a 2/1 weight ratio are physically mixed and heated in a sealed, evacuated tube at 200° C for up to 48 hours. The product is removed and washed with water and dilute hydrochloric acid to remove unreacted chromium trioxide and dried. The weight ratio of chromium trioxdide to graphite in the product is about 1.4:1. This method is described in an article in the Australian Journal of Chemistry 9, 201–5 (1956) by R. C. Croft. A commercial product thought to be made by this method is manufactured by Alfa Inorganics, Beverly, Mass.

In another method (acid reflux method) described by N. Platzer and B. de la Martiniere, Bull. Soc. Chim. France 1961, 177–180, chromium trioxide and graphite in a 4/1 weight ratio are added to refluxing glacial acetic acid at 118° C. A brown solution forms due to a chromium trioxide-acetic acid complex. After refluxing for 30 minutes the material is filtered hot, washed with glacial acetic acid and dried under vacuum for at least one day. As discussed above, chromium trioxide-graphite compounds prepared by this method have been found ineffective for dehydrocyclization of nonaromatic compounds.

The catalysts employed in the present invention are particularly applicable to the dehydrocyclization and reforming of hydrocarbons including acyclic and cyclic paraffins and olefins, particularly naphthenes and paraffins. The catalysts are particularly suitable for the reformation of paraffins containing six or more carbon atoms per molecule including n-hexane, 2-methylhexane, n-heptane, n-octane, 3-methylheptane, 2,4-dimethylhexane, n-nonane, dodecane, and the like. Some examples of naphthenes which can be reformed with these catalysts are methyl cyclopentane, cyclohexane, and the like. Some olefins can also be present in the feedstock, including 1-heptene, 2-nonene, 2,5-dimethylhexene-1, and the like. The preferred feeds are $C_6$–$C_{12}$ paraffins and $C_6$–$C_{12}$ naphthenes. The catalysts can be employed for the reformation of mixtures of paraffins and naphthenes such as are obtained from the distillation of straight run or natural gasolines. Most often, refinery streams containing such materials and boiling in the range of about 150°–400° F are used. Low sulfur-containing feeds are generally preferred. Typical reactions include the conversion of n-hexane into benzene and the conversion of 2,5-dimethylhexene-1 into paraxylene.

In utilizing the catalysts of this invention for the dehydrocyclization and reforming of the foregoing hydrocarbons, the hydrocarbons to be reformed are contacted with the catalysts of the invention at a temperature, pressure, and flow rate of feedstock to convert the nonaromatic hydrocarbons present in the feedstock to the desired reformed product. The conditions employed will vary appreciably depending upon the feedstock and other conditions.

The reaction can be conducted under vapor phase conditions at a temperature ranging from about 840°–1300° F (450°–704° C), preferably from about 900°–1100° F (480°–594° C), and a pressure ranging from about 0 to about 100 psig (0-689 kPa gage), preferably from about 0 to about 50 psig (0-345 kPa gage). The process can be conducted gas phase in the presence of an inert diluent such as nitrogen, argon, and the like. In this case, a volume ratio of diluent to hydrocarbon ranging from about 5:1 to about 25:1, preferably about 10:1 to 20:1, can be employed. The gaseous hourly space velocity (GHSV) of total feed (hydrocarbon plus diluent) can range from about 200-2000, preferably from about 750-1200, under these conditions.

Alternately, the reaction can be conducted liquid phase in the absence of a diluent. In such an event a liquid hourly space velocity (LHSV) ranging from 0.05 to 10, more preferably 0.1 to 5, can be used. Pressure used depends upon the feed and the temperature employed but will be sufficient to maintain liquid phase conditions. Thus, the pressure will be generally less than about 600 psig (4137 kPa gage) and ordinarily between about 100-400 psig (689-2758 kPa gage).

The temperature to be employed in the reforming process will be determined largely by the other operating conditions, that is, at a particular pressure, liquid hourly space velocity or gaseous hourly space velocity, the temperature is normally determined by the desired octane number of the product to be produced.

In utilizing the catalyst of this invention for dehydrocyclizing the hydrocarbon feedstock, the mode of contact employed can be by a fixed or a fluidized catalyst bed. The reaction can be carried out continuously or batchwise. In either case, the effluent is separated into components by conventional means such as fractionation, adsorption, solvent extraction, and the like. Unconverted feed can be recycled.

EXAMPLE

A series of catalysts containing chromium oxides and graphite was prepared or obtained commercially. Each catalyst was used to dehydrocyclize n-hexane.

Catalyst A was a chromium trioxide-graphite intercalate containing 58 weight percent $CrO_3$ obtained commercially (Alfa Inorganics). $CrO_3$-graphite weight ratio is 1.38:1.

Catalyst B was an experimentally produced chromium trioxide-graphite intercalate containing 58 weight percent $CrO_3$ formed by the dry method.

Catalyst C was an experimentally produced chromium trioxide-graphite intercalate containing 58 weight percent $CrO_3$ formed by the acid reflux method.

Catalyst D was a physical mixture of 58 weight percent $Cr_2O_3$ and graphite.

Catalyst E was formed by impregnating graphite with a solution containing sufficient $CrO_3$ to obtain a product containing 10 weight percent $CrO_3$ on a dry basis. The impregnated material was dried before use. The graphite used in Catalysts B, C, D, and E was SP-1 grade spectroscopic powder obtained from Union Carbide.

Analysis by X-ray diffraction established that the graphite lattices of Catalysts A, B, and C were all expanded confirming that intercalates were present in each instance.

Catalyst F was a conventional chromium oxide-alumina catalyst, commercially obtained, containing 23 weight percent $Cr_2O_3$, 75 weight percent $Al_2O_3$, and 2 weight percent P used as a control. Such catalysts are known dehydrocyclization agents.

The reaction temperatures employed and results obtained are given in the following table. Generally, in the runs conducted at atmospheric pressure, a nitrogen/n-hexane volume ratio of 18/1 was used with a total feed (diluent plus hydrocarbon) GHSV of 960. In all instances, a fixed bed tubular reactor was used and individually charged with 0.5 cc of catalyst for each run.

TABLE

| | | Dehydrocyclization of Normal-Hexane | | | |
|---|---|---|---|---|---|
| Run No. | Catalyst | Reactor Temp., °C | Conversion, Hrs. 0.5 | 2 | Percent Benzene Formed | Selectivity to Benzene, % |
| 1 | F | 500 | 21.0 | NA[a] | 13.2 | 63 |
| 2A | A | 500 | 28.5 | NA | 22.0 | 77 |
| 2B | A | 550 | NA | 40.5 | 34 | 84 |
| 3 | B | 550 | NA | 25.1 | 18.6 | 74 |
| 4 | C | 550 | NA | 2.2 | 0.2 | 8.6 |
| 5 | D | 550 | NA | 3.1 | 0.6 | 19 |
| 6 | E | 550 | NA | 4.2 | 1.9 | 45 |

[a]Not applicable.

The results show that invention catalysts A and B, Runs 2A, 2B, and 3, are clearly superior to the other catalysts tested based on conversion, production of benzene, and selectivity to benzene. The data show also that the chromium trioxide-graphite intercalate produced by the acid reflux method (catalyst C, Run 4) is ineffective for the dehydrocyclization of n-hexane. The reason for the poor results are not known but perhaps are related in some fashion to the manner of formation of the catalyst by the acid reflux method.

I claim:

1. A process for reforming nonaromatic hydrocarbons to produce a product having an increased aromatic content which comprises contacting a nonaromatic hydrocarbon-containing feed under reforming conditions of temperature and pressure in the presence of a catalyst consisting of a molecular chromium trioxide-graphite intercalation complex to convert the nonaromatic hydrocarbons present in the feed to aromatics, and withdrawing a reformate rich in aromatics, said catalyst having been prepared by heating a mixture of chromium trioxide and graphite at an elevated temperature and for a period of time sufficient to form said complex having a weight ratio of chromium trioxide to graphite of about 0.01:1 to about 2.5:1.

2. A process according to claim 1 wherein said contacting is carried out under vapor phase conditions at a temperature ranging from about 840°-1300° F (450°-704° C) and a pressure ranging from about 0 to about 100 psig, and a gaseous hourly space velocity (GHSV) ranging from about 200-2000, and further wherein said contacting is carried out in the presence of an inert diluent.

3. A process according to claim 1 wherein said contacting is carried out under liquid phase conditions at a temperature ranging from about 840°-1300° F (450°-704° C) and autogenous pressure and a liquid hourly space velocity (LHSV) ranging from 0.05 to 10.

4. A process according to claim 1 wherein said feed comprises paraffins of 6-12 carbon atoms.

5. A process according to claim 1 wherein normal hexane is converted to benzene under vapor phase conditions at a temperature in the range of about 840°-1300° F (450°-704° C) in the presence of nitrogen as an inert diluent.

6. A process according to claim 1 wherein said molecular chromium trioxide-graphite intercalation compound is prepared by (a) heating a mixture of anhydrous chromium trioxide and graphite at an elevated temperature in the range of about 175° C to about 400° C for a period of time ranging from about one hour to about 60 hours or more to form a graphite-chromium trioxide interlayer complex, (b) washing the complex thus produced with water to remove unreacted chromium trioxide, and (c) drying the resulting washed graphite-chromium trioxide interlayer complex by heating.

7. A process for reforming nonaromatic hydrocarbons to produce a product having an increased aromatic content which comprises contacting normal hexane under dehydrocyclization conditions of temperature and pressure in the presence of a catalyst consisting of a molecular chromium trioxide-graphite intercalation complex to convert the normal hexane to benzene, and withdrawing a reformate rich in benzene, said catalyst having been prepared by heating a mixture of chromium trioxide and graphite at an elevated temperature and for a period of time sufficient to form said complex having a weight ratio of chromium trioxide to graphite of about 0.01:1 to about 2.5:1.

8. A process according to claim 1 wherein said feed comprises cyclohexane.

9. A process according to claim 1 wherein cyclohexane is converted to benzene under vapor phase conditions at a temperature in the range of about 840°–1300° F (450°–704° C) in the presence of nitrogen as an inert diluent.

* * * * *